United States Patent
Billinger et al.

(10) Patent No.: US 12,127,876 B2
(45) Date of Patent: Oct. 29, 2024

(54) FUNCTIONAL TRANSCRANIAL DOPPLER ULTRASOUND AND METHODS OF USE

(71) Applicant: University of Kansas, Lawrence, KS (US)

(72) Inventors: Sandra A. Billinger, Roeland Park, KS (US); Eric D. Vidoni, Roeland Park, KS (US)

(73) Assignee: University of Kansas, Lawrence, KS (US)

( * ) Notice: Subject to any disclaimer, the term of this patent is extended or adjusted under 35 U.S.C. 154(b) by 525 days.

(21) Appl. No.: 17/284,758

(22) PCT Filed: Oct. 11, 2019

(86) PCT No.: PCT/US2019/055852
§ 371 (c)(1),
(2) Date: Apr. 12, 2021

(87) PCT Pub. No.: WO2020/077219
PCT Pub. Date: Apr. 16, 2020

(65) Prior Publication Data
US 2022/0125402 A1 Apr. 28, 2022

Related U.S. Application Data

(60) Provisional application No. 62/744,912, filed on Oct. 12, 2018.

(51) Int. Cl.
*A61B 8/08* (2006.01)
*A61B 8/00* (2006.01)
*A61B 8/06* (2006.01)

(52) U.S. Cl.
CPC .............. *A61B 8/0816* (2013.01); *A61B 8/06* (2013.01); *A61B 8/4227* (2013.01); *A61B 8/488* (2013.01); *A61B 8/5223* (2013.01)

(58) Field of Classification Search
CPC ....... A61B 8/0816; A61B 8/06; A61B 8/4227; A61B 8/488; A61B 8/5223; A61B 5/4836;
(Continued)

(56) References Cited

U.S. PATENT DOCUMENTS

2006/0100530 A1 5/2006 Kliot et al.
2016/0220850 A1 8/2016 Tyler

FOREIGN PATENT DOCUMENTS

WO  WO 2016/110804  7/2016

OTHER PUBLICATIONS

Komiyama et al., Cognitive function during exercise under severe hypoxia. Sci Rep. Aug. 30, 2017;7(1):10000. doi: 10.1038/s41598-017-10332-y. PMID: 28855602; PMCID: PMC5577198.*

(Continued)

*Primary Examiner* — Bo Joseph Peng
(74) *Attorney, Agent, or Firm* — RAY QUINNEY & NEBEKER P.C.; Paul N. Taylor

(57) ABSTRACT

A method of evaluating a cerebrovascular health of a patient includes causing a patient to exercise for an exercise duration at an exercise intensity, collecting cerebrovascular information from the patient during the exercise duration, collecting cardiovascular information from the patient during the exercise duration, correlating the cerebrovascular information to the cardiovascular information to create a correlated cerebrovascular curve, and determining a cerebrovascular health and viability for cerebrovascular therapy.

13 Claims, 4 Drawing Sheets

(58) Field of Classification Search
CPC . A61B 8/4416; A61B 5/0836; A61B 5/14553; A61B 5/021; A61B 5/0833; A61B 5/0205
See application file for complete search history.

(56) References Cited

OTHER PUBLICATIONS

PCT/US2019/055852, Feb. 3, 2020, International Search Report and Written Opinion.

* cited by examiner

FUNCTIONAL TRANSCRANIAL DOPPLER ULTRASOUND AND METHODS OF USE

CROSS-REFERENCE TO RELATED APPLICATIONS

This application is a U.S. Nationalization of PCT Application Number PCT/US19/55852, filed on Oct. 11, 2019, which claims priority and the benefit of United States Provisional Patent Application No. 62/744,912, filed on Oct. 12, 2018, which is hereby incorporated by reference in its entirety.

BACKGROUND

Responsive vascular control during exercise is critical to provide adequate blood flow and match $O_2$ delivery temporally and spatially to $O_2$ demands within and among the working muscles and other organs in the body. Compared to rest, maximal exercise may increase cardiac output up to ~8-fold with the majority of blood flow being distributed to the contracting skeletal muscle. By comparison the cerebral circulation supports only a relatively modest increase in blood flow. Unlike skeletal muscle where some volumetric expansion is tolerated during exercise, tight control over cerebral blood flow elevation is vital to avoid drastic changes in intracranial pressure which could damage the blood-brain barrier or potentially result in ischemic tissue injury and/or stroke.

Previous work has examined mean middle cerebral artery blood flow velocity ($MCA_V$) during resistance exercise and various intensities of cycling exercise. These studies found minimal-to-no difference in $MCA_V$ between the rest condition and constant-load submaximal exercise during resistance and low intensity exercise.

BRIEF SUMMARY

In some embodiments, a method of evaluating a cerebrovascular health of a patient includes causing a patient to exercise for an exercise duration at an exercise intensity, collecting cerebrovascular information from the patient during the exercise duration, collecting cardiovascular information from the patient during the exercise duration, correlating the cerebrovascular information to the cardiovascular information to create a correlated cerebrovascular curve, and determining a cerebrovascular health and viability for cerebrovascular therapy.

In some embodiments, a system for evaluating cerebrovascular function in a patient includes a respiratory monitoring device, a vascular monitoring device, an ultrasound transducer device; and a computing device. The ultrasound transducer device is configured to send and receive ultrasound pulses. The computing device is in data communication with the respiratory monitoring device, vascular monitoring device, and the ultrasound transducer device.

In some embodiments, a system for evaluating cerebrovascular function in a patient includes a nasal cannula, a blood pressure cuff, a head-mounted ultrasound transducer device; and a computing device. The computing device is in data communication with a sensor of the nasal cannula, the blood pressure cuff, and the head-mounted ultrasound transducer device. The computing device includes a hardware storage device with instructions stored thereon. The instructions, when executed by a processor of the computing device, cause the computing device to: measure an end-tidal carbon dioxide concentration ($P_{ET}CO_2$) from the nasal cannula; measure a middle cerebral artery blood flow velocity ($MCA_V$) from the head-mounted ultrasound transducer; and correlate the $P_{ET}CO_2$ and the $MCA_V$.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 3-1 is a graph showing example cerebrovascular data during low and moderate exercise intensity, according to at least one embodiment of the present disclosure;

FIG. 3-2 is a graph showing example cerebrovascular data during no and moderate exercise intensity for young and older patients, according to at least one embodiment of the present disclosure;

FIG. 3-3 is a graph showing example cerebrovascular data during no and moderate exercise intensity for a healthy patient, a mild traumatic brain injury (TBI) patient, and a moderate TBI patient, according to at least one embodiment of the present disclosure;

DETAILED DESCRIPTION

Figure 1:
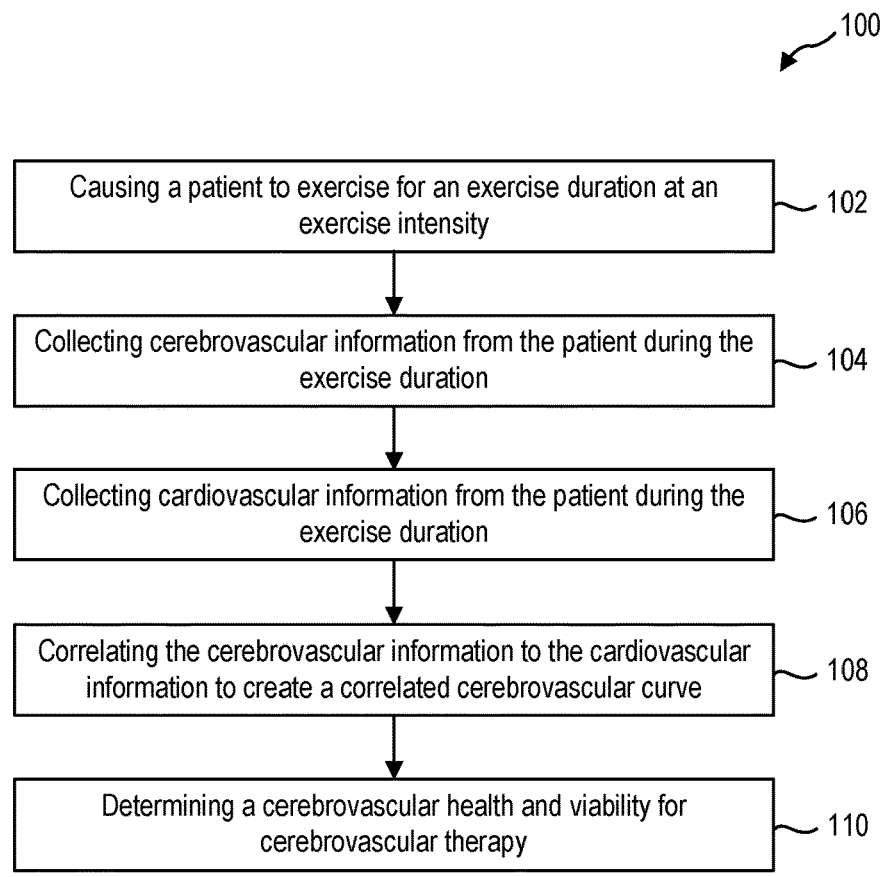
FIG. 1 is a flowchart illustrating a method of evaluating cerebrovascular function, according to at least one embodiment of the present disclosure.

This disclosure generally relates to the monitoring of cerebrovascular activity in a patient in response to exercise.

More particularly, the present disclosure relates to the use of transcranial ultrasound to measure the velocity of the middle cerebral artery (MCA) in a patient's brain. The middle cerebral artery velocity ($MCA_V$) can change in response to a physical activity load. In response to physical activity, much of the vasculature in the human body can dilate to increase flow rates and deliver a greater amount of oxygen to the muscles and brain. The MCA, however, is relatively constricted from dilation in the brain, causing the $MCA_V$ to increase to compensate for a relatively small change in cross-sectional area. This increase in velocity may be measured using an ultrasound transducer positioned near the patient's head.

The baseline $MCA_V$ and the response of the $MCA_V$ to physical activity may indicate neural health of the patient. For example, the MCA is one of the three major paired arteries that supply blood to the cerebrum. The MCA arises from the internal carotid and continues into the lateral sulcus where it then branches and projects to many parts of the lateral cerebral cortex. It also supplies blood to the anterior temporal lobes and the insular cortices. Efficient transport of blood, and hence oxygen, through the MCA is needed for healthy neural activity and for screening for physical activity-based neurotherapies.

For example, advancing age accounts for a decline in resting $MCA_V$ independent of exercise training in males, $MCA_V$ is higher in endurance trained males, supporting implementation of chronic exercise for healthy brain aging. Older adults have decreased baseline $MCA_V$ and a reduced $MCA_V$ amplitude from rest to moderate intensity exercise when compared to their younger counterparts.

In some embodiments, the $MCA_V$ is measured using a transcranial ultrasound transducer. The transcranial ultrasound transducer uses Doppler ultrasound directed at the patient's head to measure the rate and direction of fluid flow in the brain. An intensity of the Doppler ultrasound may be adjusted to alter the depth of the ultrasound penetration and measurements in the patient's head, allowing tuning of the transcranial ultrasound transducer to a particular patient. The transcranial ultrasound transducer may thereby measure the $MCA_V$ of the patient.

Measurement of the $MCA_V$ alone is insufficient to evaluate the cerebrovascular health of a patient. While the $MCA_V$ baseline may provide some indications of the cerebrovascular health of the patient, the $MCA_V$ in response to a physical activity load can provide greater information, as well as provide indications as to the viability of potential neurotherapies.

The physical activity load on a patient can be measured using one or more cardiovascular monitoring devices. In some embodiments, the physical activity load can be measured by measuring the oxygen consumption and/or carbon dioxide production of the patient during exercise with a respiratory monitoring device. For example, an enclosed chamber may allow for the measurement of changes in relative concentrations of oxygen and carbon dioxide. In other examples, a nasal cannula positioned in a patient's nasal cavity may allow for end-tidal carbon dioxide ($P_{ET}CO_2$) measurements. In other embodiments, the physical activity load is measured by heart rate measurements, such as an electrocardiogram. In other examples, the physical activity load may be measured by measuring the mean arterial blood pressure (MAP) using a compressive measurement device on the user's finger or other portion of the user's body. In yet other embodiments, the physical activity load on the patient is measured by the oxygen and carbon dioxide transport of the blood. For example, the patient's blood may be monitored during physical activity to directly monitor changes in the user's blood composition.

FIG. 1 is a flowchart illustrating a method 100 of evaluating cerebrovascular function. In some embodiments, the method 100 includes causing a patient to exercise for an exercise duration at an exercise intensity at 102. The exercise duration may be at least 1 minute, at least 2 minutes, at least 3 minutes, at least 4 minutes, at least 5 minutes, or more. For example, the exercise duration may have a build-up duration, in which the patient's heart rate, respiratory rate, or other physical activity indicator may begin to and continue to increase. The build-up duration may vary depending on the patient.

After the build-up duration, a steady-state duration of the exercise duration allows for measurement of the $MCA_V$ while the patient maintains a constant level of exertion. The exercise intensity may be selected randomly at the start of the data collection session and remain constant during the exercise duration. For example, one can use the Karvonen method to determine the appropriate heart rate (HR) range for low and moderate intensity. For example, HR range=[% exercise intensity (age-predicted HR max-resting HR)]+ resting HR. A low intensity exercise may include a HR range of 30-40% and a moderate intensity exercise may include a HR range of 45-55%.

In other embodiments, the exercise intensity is a nominal work output. For example, the exercise intensity may be at least 40 Watts (W). In other examples, the exercise intensity may be at least 60 W. In yet other examples, the exercise intensity may be at least 80 W.

In an example, a patient may be instructed to maintain a step rate of approximately 120 steps per minute throughout the entire exercise duration, and resistance can be adjusted to obtain the desired workloads and targeted HR range. In at least one example, the baseline (BL) recording lasted 90 seconds, followed by a 6-minute exercise duration at the targeted HR range. After the exercise duration, a patient may remain resting quietly to allow for measures to return to baseline values.

The method 100 includes collecting cerebrovascular information from the patient during the exercise duration at 104. In some embodiments, collecting the cerebrovascular information includes measuring the $MCA_V$ during the entire exercise duration. In other embodiments, collecting the cerebrovascular information includes measuring the $MCA_V$ during the steady-state duration only. In yet other embodiments, collecting the cerebrovascular information includes measuring the $MCA_V$ during a measurement duration that is less than and within the steady-state duration. In at least one example, the build-up duration is 120 seconds, and the steady-state duration is 240 seconds. The measurement duration may be a 90-second period during the steady-state duration that begins 30 seconds after the start of the steady-state duration.

In some embodiments, the cerebrovascular information is collected using transcranial Doppler ultrasound. The transcranial Doppler ultrasound uses ultrasound pulses to measure the velocity of fluids moving in the patient's head. For example, the ultrasound transducer may be positioned proximate or adjacent the user's head to direct ultrasound pulses at the user's head. In other examples, the ultrasound transducer may be a headband or other head-mounted device that measures fluid flow with transcranial Doppler ultrasound while worn by the patient. A head-mounted device allows the user to move more naturally during the exercise duration.

The method 100 further includes collecting cardiovascular information from the patient during the exercise duration at 106. Collecting the cardiovascular information includes measuring one or more of the user's respiratory rate, oxygen consumption, carbon dioxide production, blood oxygen transport, heart rate, blood pressure, or other cardiovascular indicators. In at least one example, collecting cardiovascular information includes positioning a nasal cannula in the patient's nasal cavity to measure a $P_{ET}CO_2$. In other examples, collecting cardiovascular information includes positioning a blood pressure cuff, clip, or other compressive measurement device on the patient to measure a mean arterial blood pressure (MAP). In other examples, collecting cardiovascular information includes measuring the patient's heart rate.

The method 100 further includes correlating the cerebrovascular information to the cardiovascular information to create a correlated cerebrovascular curve at 108. The correlated cerebrovascular curve provides the cerebrovascular information in relation to the time and intensity of the exercise and the physical activity load on the patient. The correlated cerebrovascular curve allows a clinician to evaluate the cerebrovascular response to the physical activity load of the patient and determine the cerebrovascular health and viability for cerebrovascular therapy for the patient at 110.

In some embodiments, the method 100 may further include collecting cerebrovascular information and/or cardiovascular information before the exercise duration. Collecting cerebrovascular information and/or cardiovascular information before the exercise duration may allow for the establishment of a baseline cerebrovascular information and/or baseline cardiovascular information. The baseline information may aid in calculating amplitude, response rates, and other measurements that assist in determining the cerebrovascular health of the patient and viability of cerebrovascular therapy at 110.

In at least one embodiment, the method 100 further includes exposing a patient to a mental stimulus during the steady-state duration of the exercise duration. For example, a mental stimulus may produce an associated increase in cerebrovascular activity (e.g., an increase in $MCA_V$). In some examples, the mental stimulus may include a mathematics problem, a reading task (such as a brief passage the patient is asked to read to the clinician), a verbal response to a question, visual identification tasks (such as selecting a particular color from an array or a particular shape from an array), a manual task (such as assembling a small object from parts), or other short-term mental stimulus tasks.

The mental stimulus should ideally prompt brief mental activity without substantial continuing mental activity. For example, a mental stimulus that tasks the patient with recounting a recent family dinner may prompt distraction or remind the user of other responsibilities, causing continuing mental activity. Brief, discrete mental tasks allow the user's mental activity to return to the previous state during the steady-state duration. In at least some embodiments, the mental stimulus includes a verbal instruction from a clinician or other individual conducting the evaluation that is heard by the patient. In some embodiments, the mental stimulus includes a visual or written instruction that is read by the patient.

Figure 2:
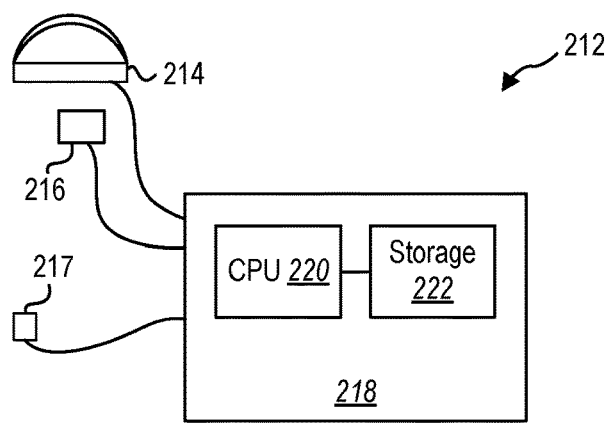
FIG. 2 is a schematic system diagram of a system for evaluating cerebrovascular function, according to at least one embodiment of the present disclosure.

FIG. 2 is a system diagram of an embodiment of a cerebrovascular evaluation system 212, according to the present disclosure. The cerebrovascular evaluation system 212 may include an ultrasound transducer 214 and at least one cardiovascular monitoring device, such as a respiratory monitoring device 216 and/or a vascular monitoring device 217, in data communication with a computing device 218. The computing device 218 includes a processor or CPU 220 and a hardware storage device 222.

In some embodiments, the ultrasound transducer 214 is positioned to direct ultrasound toward a patient's head. The ultrasound transducer 214 may be configured to measure fluid velocity and flow via transcranial Doppler ultrasound (TCD). For example, the ultrasound transducer 214 may produce an ultrasound pulse with a frequency about 2 Megahertz (MHz). The MCA has a depth of about 45-65 millimeters (mm), and the angle of the ultrasound transducer 214 may be adjusted for the individual patient. In some examples, the angle is between 45° and 60°.

The ultrasound transducer 214 may be supported at or near the patient's head by an external frame or by the patient's head itself. For example, the ultrasound transducer may be a head-mounted device that rests upon the patient's head. A headband or other head-mounted device allows the user to move more naturally during the exercise and limits distractions that may inadvertently cause a mental stimulus. In at least one example, the ultrasound transducer 214 may have a wireless communication device therein to communicate wirelessly with the computing device 218, thereby further reducing distractions and/or movement limitations on the patient.

In some embodiments, the respiratory monitoring device 216 may be an atmospheric sampling device, such as a differential oxygen/carbon dioxide analyzer, that allows for the measurement of the relative amount of oxygen and carbon dioxide in the patient's environment. For example, the patient may be confined in a closed environment chamber and the atmosphere within the chamber may be monitored to measure the amount of oxygen consumed during rest and the exercise duration. In other examples, a patient may wear a facemask that is in communication with a mobile cart having one or more sensors positioned thereon. The facemask, thereby, creates a closed respiratory environment for the patient without the need of a full environmental chamber.

In other embodiments, the respiratory monitoring device 216 is a nasal cannula that is positioned in the patient's nasal cavity to measure the $P_{ET}CO_2$ of the patient directly during rest and the exercise. The positioning of the nasal cannula may be tailored to each patient to provide optimal $P_{ET}CO_2$ measurement.

In addition to the respiratory monitoring device 216, the system includes a vascular monitoring device 217 to measure the user's heart rate, blood pressure, or other vascular information during rest and the exercise. For example, the vascular monitoring device 217 may include a finger pressure cuff to measure MAP. In other examples, the vascular monitoring device 217 may include an arm pressure cuff to measure MAP. In yet other examples, the vascular monitor device may include an electrocardiogram to measure heart rate.

The computing device 218 includes at least a processor or CPU 220 and a hardware storage device 222. The CPU 220 is in data communication with the hardware storage device 222, which has instructions stored thereon that, when executed by the CPU 220, cause the CPU 220 to perform any method or portion of a method described herein. The hardware storage device 222 may include a platen-based storage device, a solid-state storage device, or other non-transitory or long-term storage device.

Figures 1, 3:
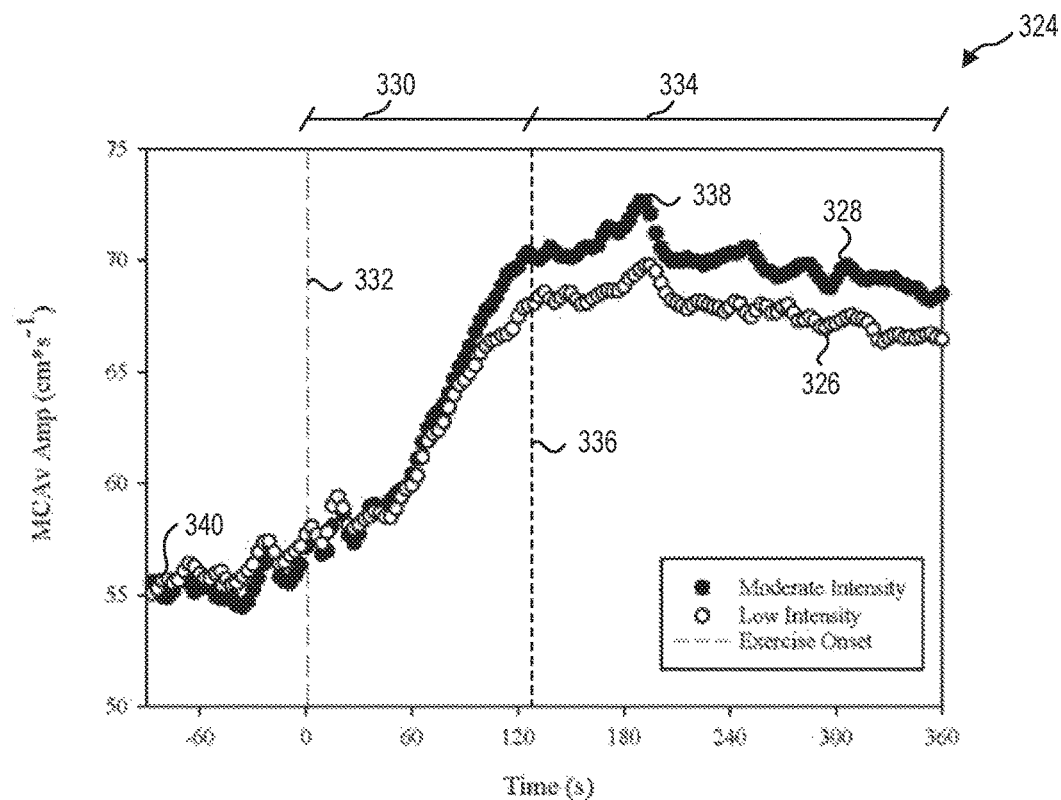
Figures 2, 3:
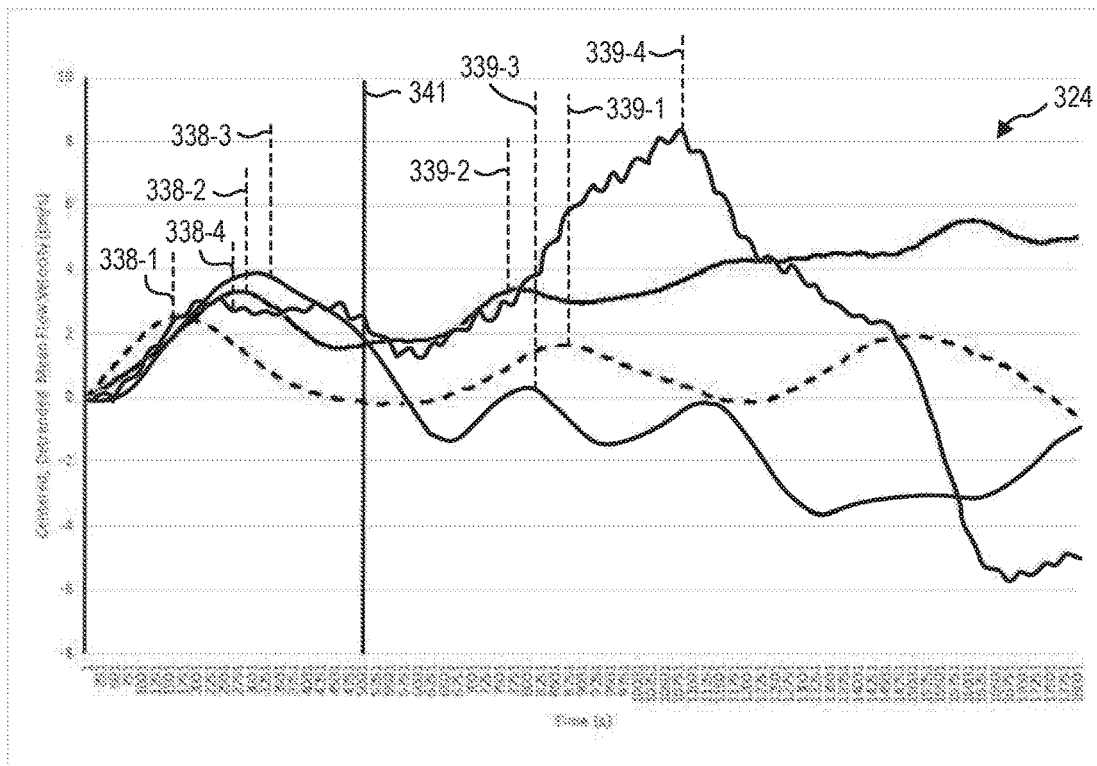
Figure 3:
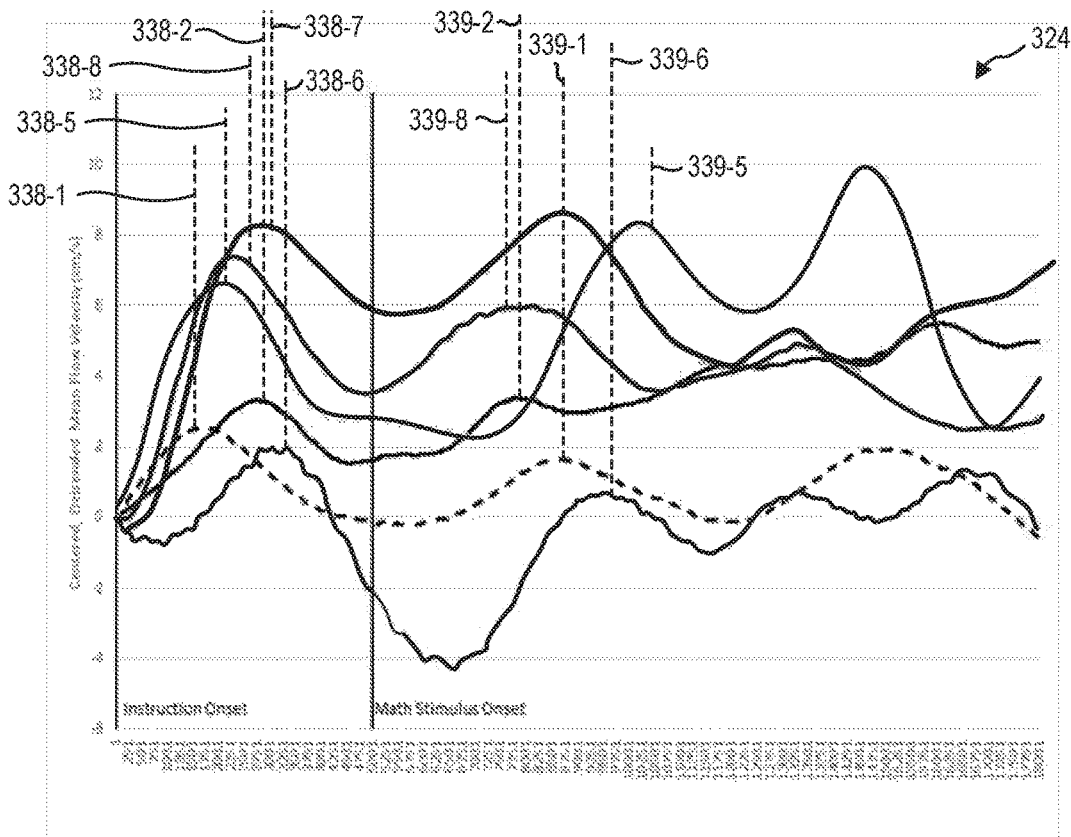

FIG. 3-1 is a graph 324 illustrating example correlated cerebrovascular curves collected by the inventors at low and moderate exercise intensities. The low exercise intensity cerebrovascular curve 326 shows a lower $MCA_V$ relative to the moderate exercise intensity cerebrovascular curve 328. Both the low exercise intensity cerebrovascular curve 326 and the moderate exercise intensity cerebrovascular curve 328 show approximately equal $MCA_V$ in a rest period 340 before the onset of exercise 332. After the onset of exercise 332, the build-up duration 330 exhibits an increase in $MCA_V$ before the $MCA_V$ begins to stabilize 336 in the steady-state duration 334.

In the illustrated example data, the build-up duration 330 is approximately 120 seconds. In other embodiments, the build-up duration 330 may be less than 30 seconds. In yet other embodiments, the build-up duration 330 may be less than 60 seconds. In further embodiments, the build-up duration 330 may be less than 120 seconds. In at least one embodiment, the build-up duration 330 may be greater than 120 seconds.

In the illustrated example data, the steady-state duration 334 is approximately 240 seconds. In other embodiments, the steady-state duration 334 may be less than 60 seconds. In yet other embodiments, the steady-state duration 334 may be less than 120 seconds. In further embodiments, the steady-state duration 334 may be less than 240 seconds. In at least one embodiment, the steady-state duration 334 may be greater than 240 seconds.

As described herein, a method of evaluating a patient's neural health may include introducing a mental stimulus during the steady-state duration 334. For example, the peak 338 exhibited in both the low exercise intensity cerebrovascular curve 326 and the moderate exercise intensity cerebrovascular curve 328 corresponds to the clinicians speaking to the patient and asking them a simple question. In each data collection session, the patient was asked a question approximately 60 seconds after the start of the steady-state duration 334. In both cases, the $MCA_V$ increased above the elevated $MCA_V$ levels from the exercise intensity.

FIG. 3-2 and FIG. 3-3 are graphs illustrating example correlated cerebrovascular curves collected by the inventors of different patient classes during moderate exercise intensity and no exercise to evaluate the response to the mental stimulus. FIG. 3-2 is a graph 324 illustrating example correlated cerebrovascular curves of young patients at a steady state moderate exercise (similar to the steady state 336 portion of FIG. 3-1) and at a steady state rest condition compared to example correlated cerebrovascular curves of older patients at a steady state moderate exercise and at a steady state rest condition.

The inventors presented the patients with both verbal instructions, to which the patients listened, and a mathematics question stimulus to provide a discrete mental stimulus. The graph begins at the onset of the verbal instructions, and the $MCA_V$ response varies based on the activity level and age of the patient. The young patient exercise $MCA_V$ peak 338-1 illustrated the most rapid $MCA_V$ response to the verbal instructions. For comparison, the young patient rest $MCA_V$ peak 338-2 was delayed. The older patient shows a delayed response in the older patient exercise $MCA_V$ peak 338-3 versus the older patient rest $MCA_V$ peak 338-4.

The relative response times invert when the mathematics mental stimulus 341 is introduced. The most rapid response is the non-verbal young patient rest $MCA_V$ peak 339-2, which was measured before the non-verbal young patient exercise $MCA_V$ peak 339-1. The older patient also inverted in response order, with the non-verbal older patient exercise $MCA_V$ peak 339-3 being detected before the non-verbal older patient rest $MCA_V$ peak 339-4. It should be noted however, that in both instances, the younger patient exhibited overall faster responses to both the verbal stimulus and the non-verbal stimulus.

FIG. 3-3 is a graph comparing the young patient exercise and rest $MCA_V$ responses with those of patients with a mild traumatic brain injury (TBI) and a moderate TBI, respectively. Again, the healthy young patient illustrates the fastest overall $MCA_V$ responses with the young patient exercise $MCA_V$ peak 338-1 and young patient rest $MCA_V$ peak 338-2. The mild TBI patient exercise $MCA_V$ peak 338-5 is the next fastest response, while the moderate TBI patient exercise $MCA_V$ peak 338-7 is later than the moderate TBI patient rest $MCA_V$ peak 338-8. This slower response in the moderate TBI patient exercise $MCA_V$ peak 338-7 is similar to the $MCA_V$ response of the older patient described in relation to FIG. 3-2.

The $MCA_V$ response to the non-verbal stimulus, again, shows the fastest overall response in a healthy patient (339-1, 339-2), with the non-verbal mild TBI patient exercise $MCA_V$ peak 339-5 and non-verbal mild TBI patient rest $MCA_V$ peak 339-6 exhibiting a response that is nearly twice as long as the non-verbal young patient rest $MCA_V$ peak 339-2. While the non-verbal moderate TBI patient rest $MCA_V$ peak 339-8 exhibits a similar response to the non-verbal young patient rest $MCA_V$ peak 339-2, the non-verbal moderate TBI patient exercise $MCA_V$ peak 339-7 is delayed over the non-verbal young patient exercise $MCA_V$ peak 339-1.

Figure 4:
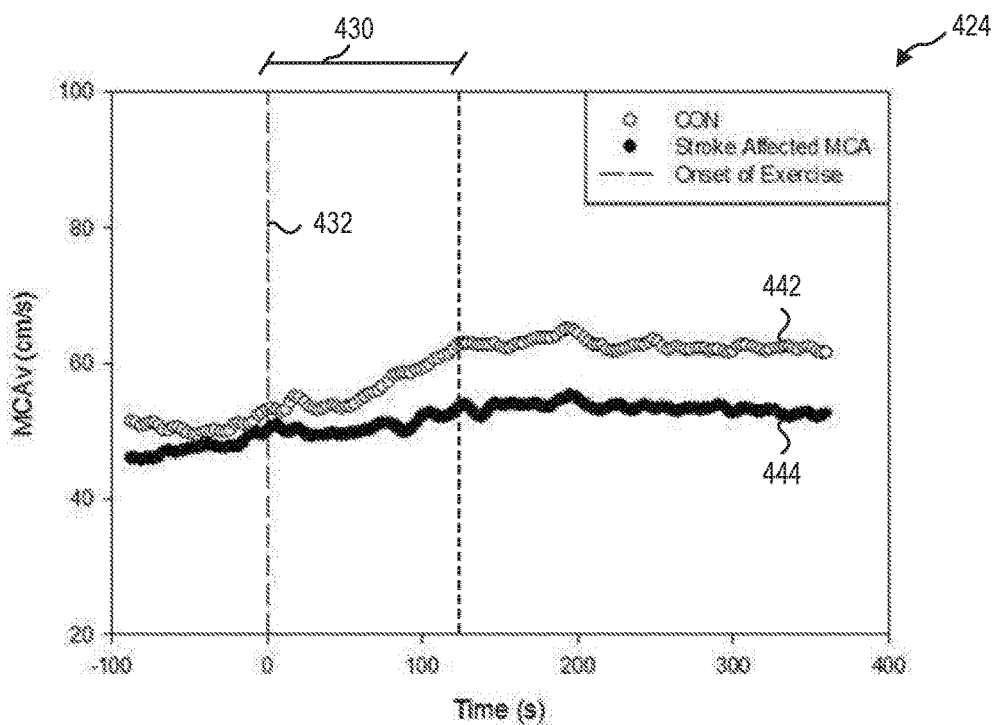
FIG. 4 is a graph illustrating example cerebrovascular data of a healthy patient compared to a stroke-affected patient, according to at least one embodiment of the present disclosure.

FIG. 4 is a graph 424 illustrating example correlated cerebrovascular curves collected by the inventors for a healthy patient and a stroke-affected patient. The healthy patient curve 442 illustrates an increase in the $MCA_V$ from the onset of exercise 432 through the build-up duration 430 that is similar to the low exercise intensity curve of FIG. 3. The stroke-affected curve 444 illustrates a suppressed effect during the build-up duration 430 and an overall lower $MCA_V$ both before the onset of exercise 432 and after. Individuals with healthy neural activity are therefore distinguishable from stroke-affected individuals by evaluating the shape and amplitude of the $MCA_V$ data.

Figure 5:
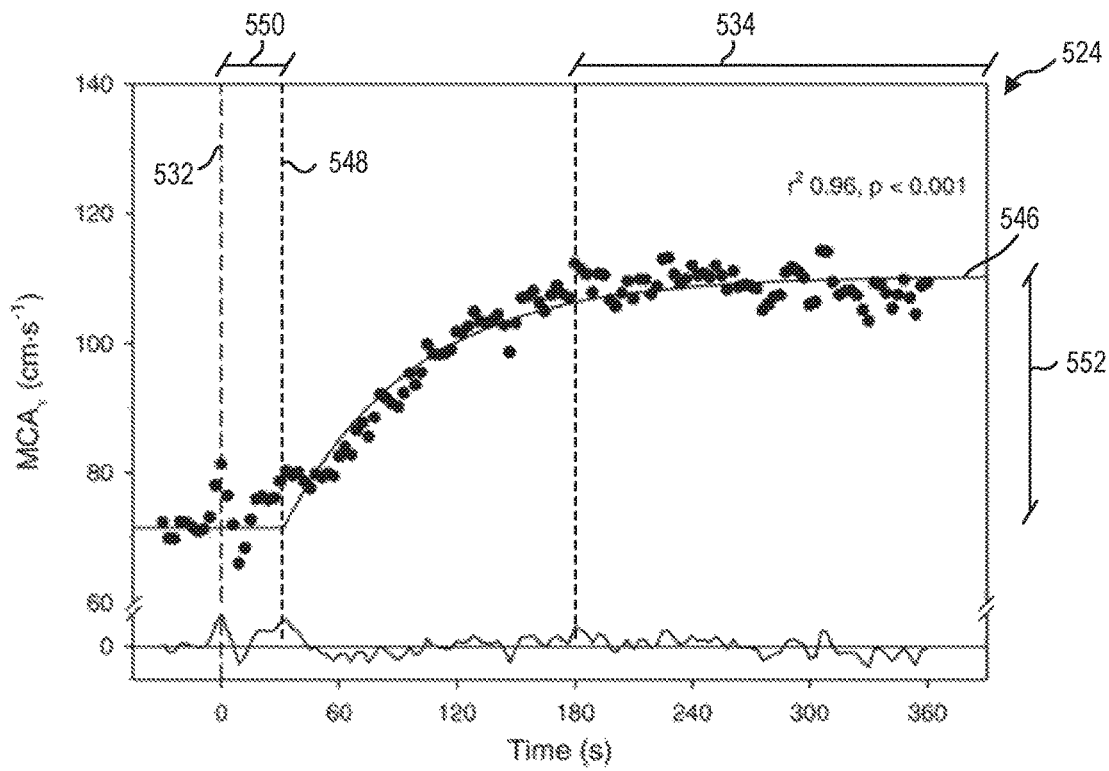
FIG. 5 is an example curve fitting of cerebrovascular data of a healthy patient, according to at least one embodiment of the present disclosure.

FIG. 5 is a graph 524 illustrating a time delay (τ) 550 and amplitude 552 of a correlated cerebrovascular curve 546. A measured correlated cerebrovascular curve 546 includes a time delay 550 from the onset of exercise 532 to an arterial response 548. The arterial response 548 is the point at which the $MCA_V$ begins increasing from the rest baseline prior to the onset of exercise 532. After the time delay 550, the $MCA_V$ begins increasing until the steady-state duration 534. The difference between the $MCA_V$ at the onset of exercise 532 and the $MCA_V$ during the steady-state duration 534 is the amplitude 552 of the correlated cerebrovascular curve 546. The amplitude has been measured to be greater amongst relatively younger individuals and amongst individuals with higher estimated $VO_2$ Max values.

In some embodiments, determining the neural health of a patient includes comparing a correlated cerebrovascular curve, such as shown in FIG. 5 against known cerebrovascular curves of individuals with similar age and/or $VO_2$ Max values. The measured data may be fit to a curve according to:

$$MCA_V(t) = BL + Amp(1 - e^{-(t-TD)/\tau})$$

where $MCA_V(t)$ is the $MCA_V$ at any point in time, BL is the baseline before the onset of exercise, Amp is the peak amplitude of the response, TD is the time delay proceeding the increase in $MCA_V$, and τ is the time constant. Mean response time (MRT) is calculated as the sum of the model derived τ and TD. The total exercising $MCA_V$ response (Tot) was calculated as the sum of BL and Amp. Time-to-63% of the steady-state response was assessed as a model-independent measure of the response. In some examples, the response to exercise is calculated as a difference between the baseline $MCA_V$ and exercise $MCA_V$. The baseline $MCA_V$ value and exercise $MCA_V$ value are an average over a period of time during the rest duration and steady-state duration, respectively. For example, the baseline and exercise $MCA_V$ values may be averaged over a period up to 20 minutes.

Figure 6:
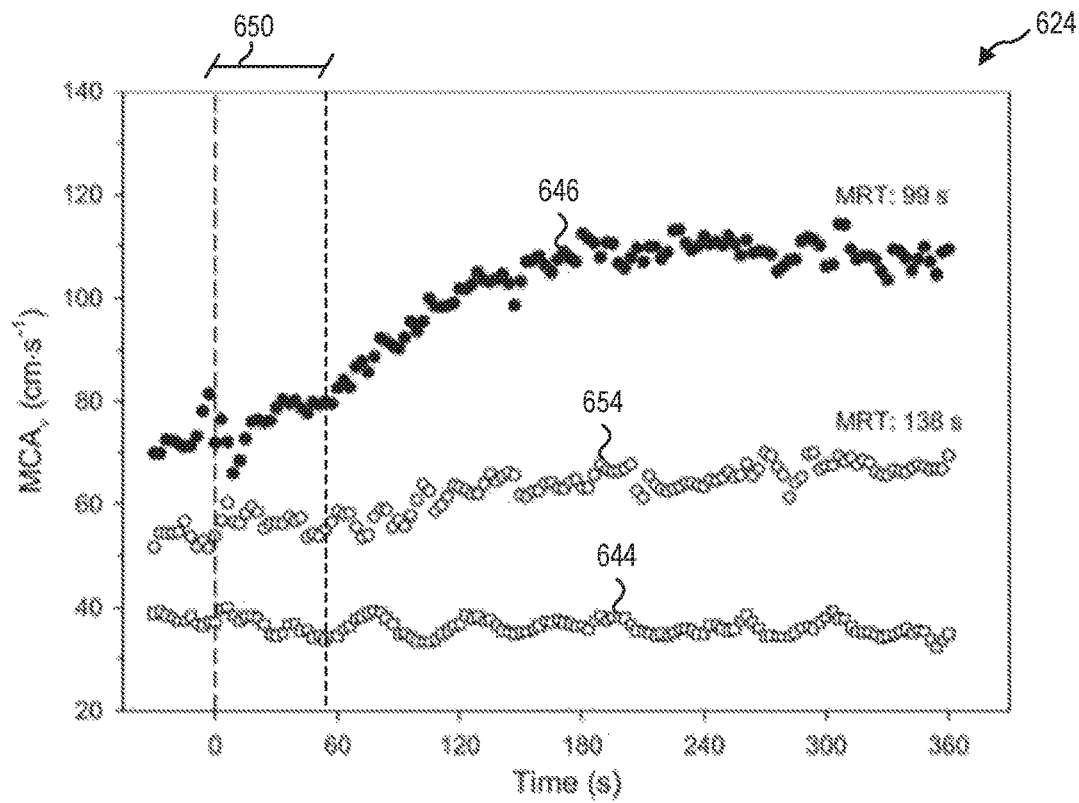
FIG. 6 is a comparison of cerebrovascular data during exercise from a young healthy patient, an older healthy patient, and an older stroke-affect patient, according to at least one embodiment of the present disclosure.

For example, FIG. 6 is a graph 624 comparing example correlated cerebrovascular curves collected by the inventors for a young patient, an older patient, and a stroke-affected patient. The top correlated cerebrovascular curve 646 is the correlated cerebrovascular curve 546 of FIG. 5 measured from a healthy 23-year-old patient. The lower correlated cerebrovascular curve 644 is the stroke-affected correlated cerebrovascular curve 444 of FIG. 4 measured from a 65-year-old patient with a stroke history. The middle correlated cerebrovascular curve 654 is a measured correlated cerebrovascular curve of a healthy 66-year-old patient. The time delay 650 is equivalent across the three correlated cerebrovascular curves 646, 654, 644 despite the amplitudes and the mean response times being different.

The mean response time (MRT) is extended for older individuals. For example, the top correlated cerebrovascular curve 646 of the 23-year-old patient has a MRT of 99 seconds. Meanwhile the middle correlated cerebrovascular curve 654 of the 66-year-old patient has a MRT of 138 seconds. In some embodiments, calculating the MRT of a measured correlated cerebrovascular curve may assist in evaluation of cerebrovascular health and the viability for cerebrovascular therapies.

In at least one embodiment of the present disclosure, a method allow for the measurement and evaluation of a patient's cerebrovascular response to exercise. The measured cerebrovascular response can be correlated to the physical load on the patient to evaluate the cerebrovascular health of the patient, as well as the suitability of the patient for exercise-based cerebrovascular therapy to improve brain health.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method of evaluating cerebrovascular function of a patient during exercise for an exercise duration at an exercise intensity, the method comprising:
   introducing a mental stimulus to the patient during the exercise duration;
   collecting cerebrovascular information including measuring a MCAv from the patient during the exercise duration and mental stimulus using an ultrasonic transducer;
   collecting cardiovascular information from the patient during the exercise duration and mental stimulus;

correlating the cerebrovascular information to the cardiovascular information to create a correlated cerebrovascular curve; and determining a cerebrovascular health and viability for cerebrovascular therapy.

2. The method of claim 1, wherein the cerebrovascular information consists of is the MCAv.

3. The method of claim 2, collecting the MCAv using the ultrasound transducer.

4. The method of claim 1, the ultrasound transducer being a head-mounted ultrasound transducer.

5. The method of claim 1, the exercise duration being at least 2 minutes.

6. The method of claim 1, the exercise duration including a steady-state duration of at least 1 minute.

7. The method of claim 1, the mental stimulus including a question having a discrete answer.

8. The method of claim 1, the mental stimulus being introduced during a steady-state duration of the exercise duration.

9. The method of claim 1, further comprising identifying a cerebrovascular response to the mental stimulus.

10. The method of claim 1, the exercise intensity being at least 40 Watts.

11. The method of claim 1, determining the viability for cerebrovascular therapy including measuring a mean response time.

12. The method of claim 1, determining the viability for cerebrovascular therapy including comparing the correlated cerebrovascular curve to one or more correlated cerebrovascular curves of patients of similar age.

13. The method of claim 1, determining the viability for cerebrovascular therapy including comparing the correlated cerebrovascular curve to one or more correlated cerebrovascular curves of patients of similar VO2 Max.

* * * * *